United States Patent [19]

Rol

[11] Patent Number: 4,598,984
[45] Date of Patent: Jul. 8, 1986

[54] CONTACT LENS ARRANGEMENT FOR OPTICALLY EXAMINING AN EYE AND TREATING IT BY LIGHT IRRADIATION

[75] Inventor: Pascal Rol, Gunten, Switzerland
[73] Assignee: Lasag AG, Thun, Switzerland
[21] Appl. No.: 687,214
[22] Filed: Dec. 28, 1984
[30] Foreign Application Priority Data Jan. 30, 1984 [FR] France .................. 84 01528

[51] Int. Cl.⁴ .................. A61B 3/00; G02C 7/04
[52] U.S. Cl. .................. 351/219; 351/160 R
[58] Field of Search ............... 351/160 R, 160 H, 219, 351/161, 162

[56] References Cited

U.S. PATENT DOCUMENTS 4,065,208  12/1977  Curry .................. 351/219

FOREIGN PATENT DOCUMENTS 0059159   9/1982   European Pat. Off. .
0092513  10/1983   European Pat. Off. .
1175511   3/1959   France .
2304315  10/1976   France .
0012885   of 1913  United Kingdom .

Primary Examiner—John K. Corbin
Assistant Examiner—Scott J. Sugarman
Attorney, Agent, or Firm—Pollock, Vande Sande & Priddy

[57] ABSTRACT

A contact lens arrangement is described for optically examining an eye and/or treating it by light irradiation, in particular the retina, in the region of or away from the optical axis of the eye.

The contact lens arrangement comprises a Goldmann lens having a plane entry surface and a spherical exit surface, applied to the cornea of the eye, and a compensating element, e.g. a prism, having an entry surface. The compensating element is fixed to the entry surface of the Goldmann lens and its function is to produce an astigmatism opposite to that of the eye with an incident light beam, entering through its entry surface.

This contact lens arrangement enables very accurate focusing of the beam on to a particular point inside the eye.

9 Claims, 5 Drawing Figures

CONTACT LENS ARRANGEMENT FOR OPTICALLY EXAMINING AN EYE AND TREATING IT BY LIGHT IRRADIATION

BACKGROUND OF THE INVENTION

1. Field of the Invention

This invention relates to a contact lens arrangement for optically examining the interior, in particular the retina, of an eye and for treating it by light irradiation.

The eye, in particular the diaphragm, the crystalline and the retina, may be affected by several diseases. To diagnose the affection, the interior of the eye must be optically inspected in an accurate way.

2. Prior Art

Several methods of examination are known. The best images to be had are obtained by using a contact lens which, when applied to the eye, causes minimum distortion of the light beam received from the point under observation, or working point, inside the eye, e.g. a Koeppe or a Goldmann lens, described in particular in a publication entitled "Gonioscopie und Goniofotographie", authored by Winfried Müller and Hans-Peter Brandt, and published by Ferdinand Enke in Stuttgart in 1979.

A Koeppe contact lens has a rounded entry surface and a substantially spherical exit surface adapted to be applied to the cornea. A Goldmann contact lens is more particularly designed for examining the retina and has a plane entry surface and a spherical exit surface. It may also have one or several reflecting surfaces acting as mirrors, enabling indirect examination of the interior of the eye.

Ophthalmologists particularly appreciate these kinds of contact lens for examinations, especially the second, as they are easy to handle and comfortable in use. However, the quality of the image they produce gradually deteriorates as the distance of the point under observation from the the optical axis of the eye increases.

While such a contact lens is useful for observing the interior of an eye, it is essential for treating a retina by irradiation. But in this latter case, because the operating conditions are different from those for observation, the lens must meet stricter requirements.

Treating the interior of an eye by irradiation is achieved by focusing on to the affected area, or onto a part of that area, an intense beam of coherent light. This beam can be produced for example by an Nd-YAG or Argon laser.

For the treatment to be effective and harmless, the beam reaching the working point must be accurately focused and strongly convergent, i.e. the angle made by the light rays at their innermost end should be wide. Good focusing enables the working point to be accurately pin-pointed and considerable energy to be concentrated thereon. Strong convergence enables the working point to be accurately pin-pointed in depth. As a result also, the energy density of the beam decreases rapidly away from the working point, thereby reducing the risk of damaging healthy parts of the eye. The focusing of the light beam would also be better if the spherical aberrations and the astigmatisms of the optical system through which the beam has to travel, i.e. the contact lens and the eye, are slight. However, these flaws usually increase with the diameter or the convergence of the incident beam. These two conditions are thus contradictory and a compromise must be found for each particular use. A Goldmann lens does not solve satisfactorily the problem associated with the wideness of the angle of the light beam, and even less so that associated with astigmatism. Thus, while such a lens will always be suitable for retina examination, retina treatment by irradiation with such a lens will only be satisfactory at points close to the axis of the eye. For other points of the retina the difficulties increase the further removed they are from the axis.

Various improved, more effective, versions have been proposed for the Goldmann lens, e.g. the so-called Abraham lens arrangement consisting of a mirror-less Goldmann lens having a plano-convex lens of mineral glass fitted off-centre to its entry surface. This modification enables the angle of the beam to be widened but tends also to enhance the aberrations. Another example is the so-called Roussel lens arrangement, a more recent development described in the specification of our European patent application 82810044.6. In this lens arrangement the light receiving surface constitutes a wave surface for the beam. As a result, the aberrations are reduced but the width of the angle of the beam is unaffected.

All atempts made to improve the Goldmann lens were aimed at the contact lens itself, without considering the optical properties of the eye it was designed to examine or irradiate. Thus even a flawless contact lens would not enable a light beam to be perfectly focused on a point of the retina remote from the axis of the eye. To reach this point, the beam must travel through the different parts of the eye, in particular the crystalline which has an astigmatism that worsens when viewed with a high angle of incidence. This causes the beam to deteriorate. No contact lens, Goldmann or other, takes this phenomenon into consideration. This is a serious flaw in known lenses designed to treat the retina at points situated away from the axis of the eye.

SUMMARY OF THE INVENTION

A main object of the invention is to provide a contact lens arrangement for examining and treating by irradiation various internal parts of an eye, in particular the retina, which does not suffer from the above drawbacks.

To this end, the invention provides a contact lens arrangement for optically examining an eye and treating it with an incident light beam, comprising a principal element having a plane entry surface, disposed in use at right angles to the beam, and an exit surface adapted to be applied to the eye and to focus said beam onto a working point inside the eye, and a compensating element applied to the entry surface of the principal element and adapted to produce within the lens arrangement an astigmatism opposite to that of the eye.

One advantage of the contact lens arrangement according to the invention is that it enables an incident light beam to be accurately focused on one point of the retina in spite of the optic flaws of the parts of the eye the beam goes through.

BRIEF DESCRIPTION OF THE DRAWINGS

In the accompanying drawings, given by way of example.

Corresponding elements in the Figures have been given the same reference numerals.

DETAILED DESCRIPTION

Figure 1:
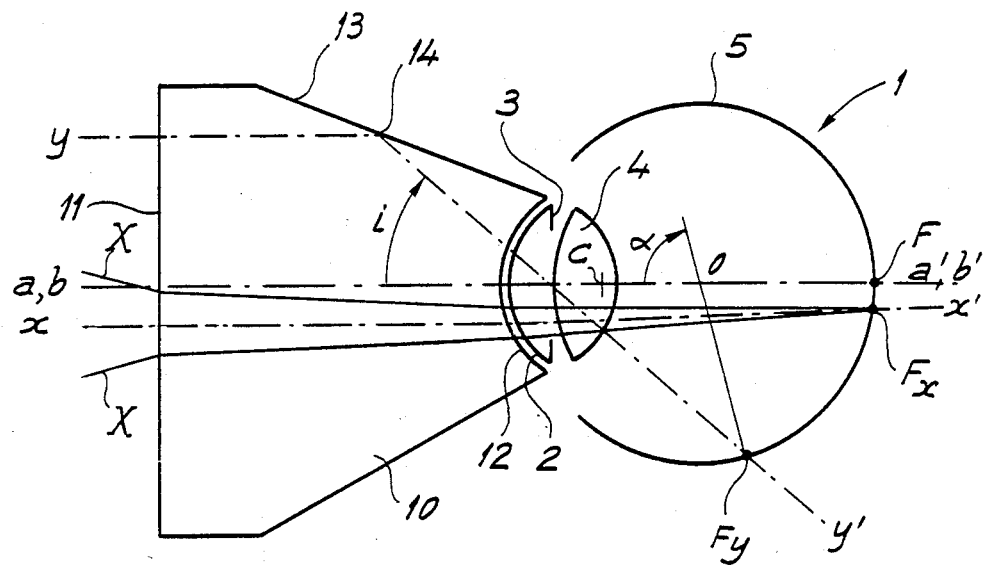
FIG. 1 is a cross-section along a longitudinal plane of symmetry showing, schematically, an eye to the cornea of which a Goldmann lens has been applied.

The eye, 1, shown in FIG. 1 is a ball having an axis of symmetry aa' and having successively, from the exterior to the interior of the eye, a cornea 2 through which light rays enter, an iris 3 whose aperture regulates the amount of light entering, a crystalline lens 4, and a spherical retina 5 having a centre O and through which extends axis aa' at a point F. For a better understanding of the invention, reference will first be made to a Goldmann mirror contact lens, also shown in FIG. 1. This lens, 10, has a plane entry surface 11, a concave exit surface 12 applied to the cornea 2, and a reflecting surface 13. Other reflecting surfaces, not shown, are provided around the lens. The angle between a reflecting surface 13 and the entry surface 11 depends on the point of the retina at which light is to be aimed. This angle may range from 50° to 80°. The straight line that is perpendicular to entry surface 11 and which passes through the centre of curvature C of exit surface 12 defines an axis of symmetry bb' of contact lens 10. In the case of FIG. 1, axes aa' and bb' coincide. Lens 10 is so sized that it can be moved over cornea 2 and hence move, within limits, the point to be examined or the point to be treated (or working point) inside the eye. Axis bb' then pivots or hinges round centre C.

The field of application of the Goldmann lens is quite broad, as it practically has access to all essential points inside the eye, for both examination and treatment. Although the effectiveness of the lens is good for points located close to the cornea, it is poor for those located on retina 5 away from axis aa', for reasons which will be given later.

A main object of the invention being to provide a modified Goldmann lens arrangement enabling examination and particularly treatment by irradiation of any point of retina 5 under good conditions, FIG. 1 shows the path of light in a Goldmann lens for two typical points on the retina. The first point, $F_x$, in FIG. 1 corresponds to a point close to axis aa' of the eye. To reach this point, an incident light beam X, having an axis xx', must enter Goldmann lens 10 perpendicularly to entry surface 11, at a certain distance from axis aa' and go directly, without reflection, through lens 10 and eye 1. The second point, $F_y$, corresponds to a point remote from axis aa'. The angle α formed by axis aa' and the straight line joining point $F_y$ to centre O of retina 5 may exceed 90°. To reach point $F_y$, a light beam Y, of which only axis yy' is shown, must, after entering lens 10 perpendicularly to surface 11, be completely reflected by surface 13 at a point 14 in order to penetrate eye 1 with an angle of incidence i. To each area of retina 5 remote from axis aa' corresponds a particular slant of surface 13 with respect to surface 11 of lens 10. This is why a Goldmann lens best has several reflecting surfaces or sides with different slants or slopes.

Since the eye is not a perfect optical system, even a flawless contact lens would not enable a light beam to be focused on one point, but at best only within a circle of diffusion having a more or less reduced diameter since the astigmatism of an eye is that much greater when the angle of incidence i of a light beam passing through the crystalline lens is high. To achieve accurate focusing, the contact lens must therefore have an astigmatism opposite to that of the eye.

There are several models of the eye, e.g. the Gullstrand-Legrand model and the Littmann model, which enable its optical properties to be accurately described. The eye, like any spherical optical surface, has an astigmatism which can be decomposed into a sagittal part and a tangential part. Each part is defined by its focal distance, measured, for example, from the entry surface of the eye. The focal distance corresponding to the sagittal part is termed S and that corresponding to the tangential part is termed T.

Theoretical considerations and tests have shown that is is possible to devise a compensated contact lens arrangement having the required opposite astigmatism by fitting to the entry surface of a Goldmann lens a compensating element of simple shape, which is easy and inexpensive to produce.

The compensating element modifies the point aimed at with a Goldmann lens. This modification is however slight and can be compensated by a slight alteration, to the extent of a few degrees, of the slant of the reflecting surface. In practice, it is always possible to make or to find, for each point aimed at, a suitable Goldmann lens. Indeed, there are standard lenses whose reflecting surfaces have a slant, with respect to the entry surface, lying between 50° and 80°.

Figure 2A:
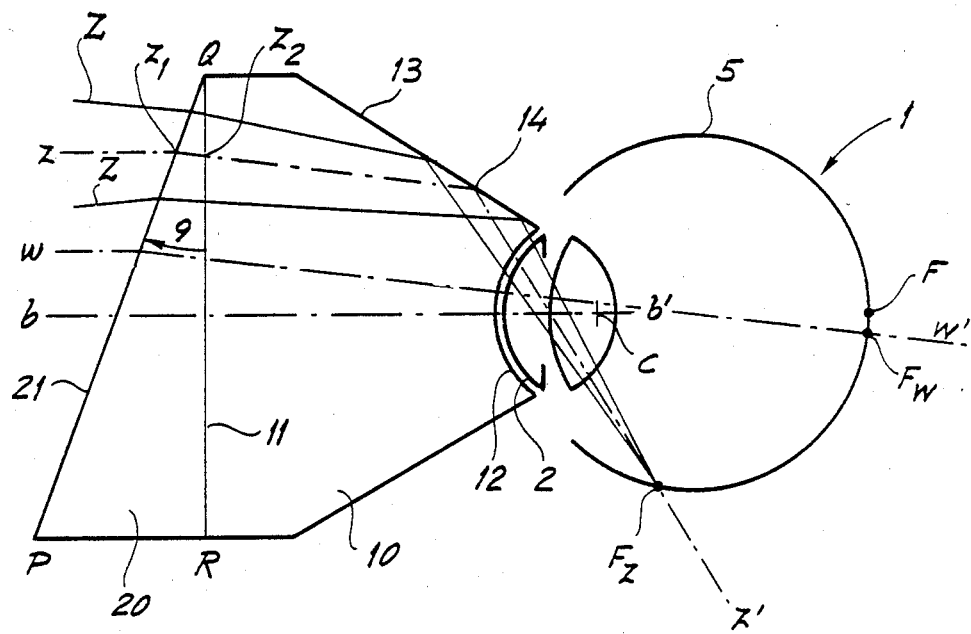
FIGS. 2a to 2d are similar views of several forms of contact lens arrangements according to the invention.

In the compensated contact lens arrangement shown in FIG. 2a, the compensating element is a prism 20 whose intersection with the plane of the Figure is a triangle PQR, right-angled at R, and having edges perpendicular to the plane of the drawing. This prism is positioned in such a way that, on the one hand, its surface contacting points Q and R is applied against the entry surface 11 of Goldmann lens 10 and, on the other hand, point Q lies on the same side, with respect to axis bb', as reflecting surface 13. The plane of prism 20 containing points P and Q thus becomes the entry surface 21 of the compensated contact lens arrangement.

FIG. 2a also shows the path of a light beam Z having an axis zz', the assumption being that Goldmann lens 10 and prism 20 are made of the same material. The direction of the incident beam is chosen parallel to axis bb' of the contact lens arrangement. Axis zz' of the beam enters prism 20 obliquely with respect to surface 21, at a point $z_1$ of this surface. The refractive index of the prism (about 1.5) being greater than that of air (equal to 1), the light rays of beam Z are refracted as they travel through surface 21. After this refraction, axis zz' passes through entry surface 11 of Goldmann lens 10, again obliquely, at a point $z_2$. This time however the beam is not refracted as both media on opposite sides of surface 11 are assumed to be identical. Axis zz' then reaches a point 14 on surface 13 where it is subjected to total reflection, whereupon it enters eye 1 and reaches retina 5 at a point $F_z$.

In the compensated contact lens arrangement shown in FIG. 2a, the compensating element is prism 20. As is well known, such a prism has, as far as light beam Z is concerned, an astigmatism. This astigmatism depends on the angle q at point Q of triangle PQR and on the distance e, not shown, travelled by the light beam rays between entry surface 21 and exit surface 12 of the contact lens arrangement of refractive index n.

In $q = \arc \sin [(T-S)/(T+e-(S+e)/n^2)]^{\frac{1}{2}}$, S and T being, as mentioned earlier, the focal distances corresponding respectively to the sagittal and tangential parts of the astigmatism, then the astigmatism of the prism becomes the exact opposite of that of the eye, thus achieving the required correction of the Goldmann lens. If the material used is a plastic for which n equals 1.5, angle q is roughly 20° for the point $F_z$ aimed at in FIG. 2a.

Point $z_1$ of axis $zz'$ is located between point Q and axis $bb'$, on surface 21. Length e of the path of the light rays inside the contact lens being dependent on point $z_1$, there is a precise value for angle q for each position of point $z_1$. This value makes it possible to achieve optimal focusing of the incident light beam Z on point $F_z$ of retina 5.

The compensated contact lens arrangement in FIG. 2a may of course be made in one piece. Also, only that part of prism 20 which receives light beam Z is operative. The remainder of the prism may have any shape. In particular, the angle at point R of the triangle at the base of the prism may have a value other than 90°.

Figure 2B:
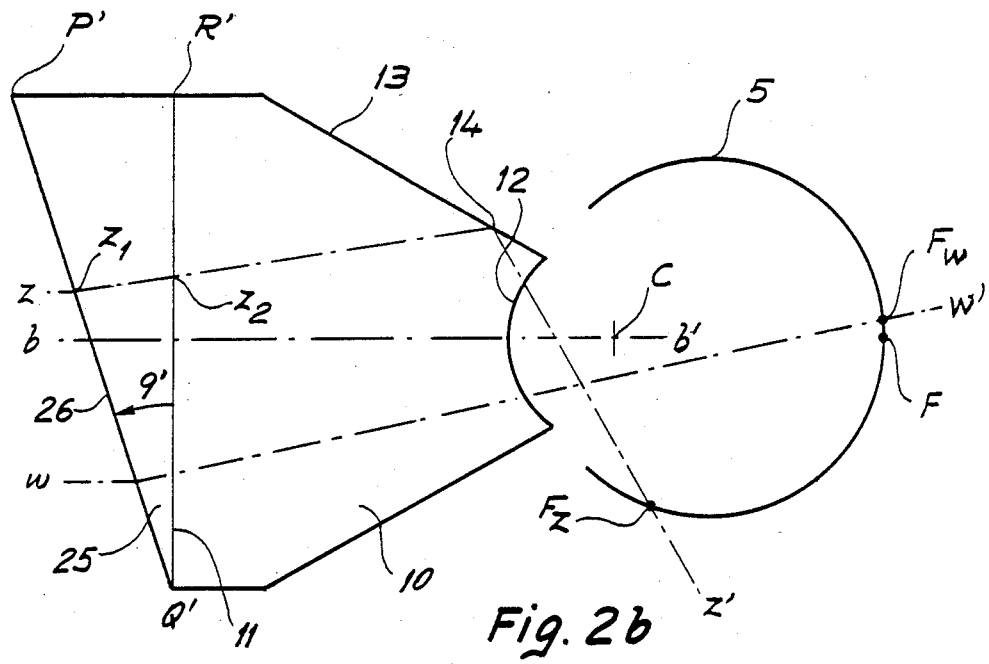

The compensated contact lens arrangement shown in FIG. 2b is similar to that shown in FIG. 2a except that it uses by way of compensating element a prism 25 having a triangular base $P'Q'R'$, right-angled at $R'$, which is so positioned that points $P'$ and $R'$ lie on the same side, with respect to axis $bb'$, as the reflecting surface 13 of Goldmann lens 10. The positioning of prism 25 on the Goldmann lens thus amounts to a rotation of prism 20° through 180° about an axis parallel to axis $bb'$.

Prism 25 has an entry surface 26 on which impinges a light beam having an axis $zz'$. This axis passes through points $z_1$, $z_2$ and 14 to reach retina 5 at point $F_z$, as in FIG. 2a. The different positioning of the compensating prism, however, causes point $F_z$ to be slightly more distant from point F of eye 1 than in FIG. 2a if the same angle is used for mirror 13. By modifying the slant of the mirror the beam can be made to reach point $F_z$ of FIG. 2a.

For prism 25 to have an astigmatism exactly opposite to that of the eye, angle $q'$ at point $Q'$ of triangle $P'Q'R'$ must have a well defined value, given by the same relationship as that for angle q.

The contact lens arrangements of FIGS. 2a and 2b may also be used in transparency with much smaller angles q or $q'$ but still given by the same relationship as before. In this type of use, a light beam, having an axis $ww'$, travels through the contact lens arrangement without being reflected by surface 13 of the Goldmann lens. A point $F_w$ of the retina, located close to the axis of the eye, can be reached. The light beam that has $ww'$ as its axis reaches entry surfaces 21 or 26, shown in FIGS. 2a and 2b, under the same angle as the beam that has $zz'$ as its axis and, in the contact lens arrangement, it follows a path parallel to the part of axis $zz'$ joining points $z_1$ and 14.

Figure 2C:
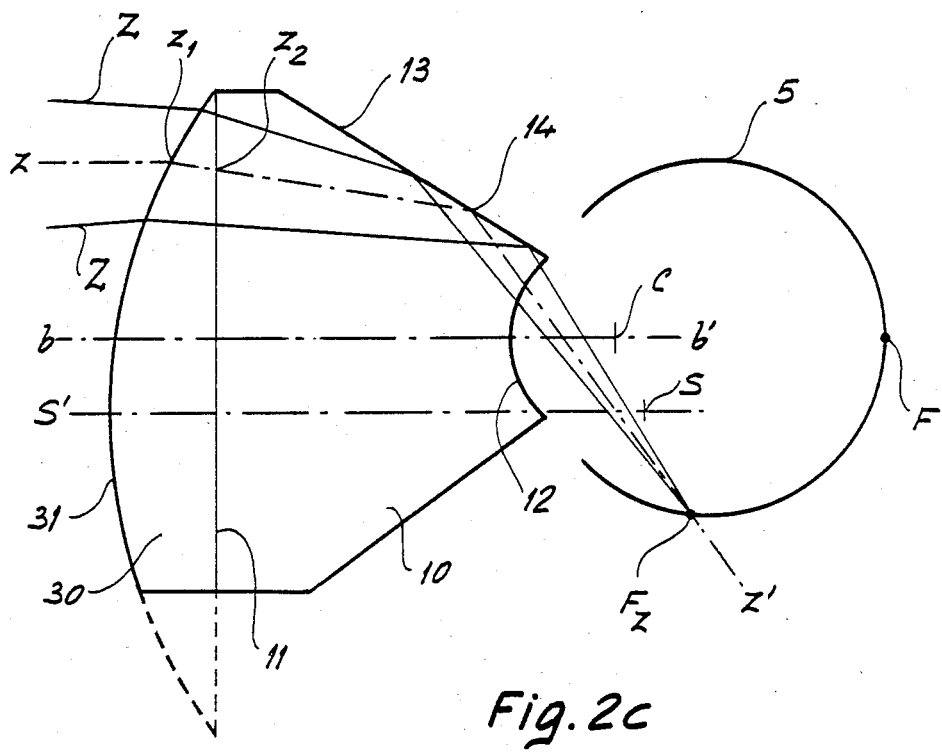

In the compensated contact lens arrangement shown in FIG. 2c, the compensating element consists of at least a portion of a plano-convex lens 30 having a plane surface and a spherical surface 31. The plane surface of lens 30 is applied against the entry surface 11 of the Goldmann lens. Spherical surface 31 of lens 30 constitutes the entry surface of the contact lens arrangement. This surface is defined by the position of its centre of curvature S, with respect to Goldmann lens 10, and by its radius of curvature. A straight line, perpendicular to the plane surface of lens 30 and passing through centre S, defines axis $SS'$ of the lens. This axis is parallel to axis $bb'$. Certain circumferential parts of lens 30 may be truncated as shown with dotted lines in FIG. 2c.

For an incident beam Z, having an axis $zz'$ parallel to axis $bb'$ up to entry surface 31, optics formulae, known as the Coddington equations and which may for example be found in pages 186 and 187 of a book entitled "Lens Design Fundamentals" by Rudolph Kingslake, published by Academic Press, New York, in 1978, enable firstly the radius of curvature of surface 31 and secondly the distance between axes $SS'$ and $zz'$ (and hence between axes $SS'$ and $bb'$) to be calculated. Several solutions are possible. If the material is plastic, the above radius and distance may measure, e.g., respectively, 42 and 8 mm, point S being located on the side opposite to surface 13 with respect to axis $bb'$.

An incident light beam Z, having an axis $zz'$, on reaching the contact lens arrangement parallel to axis $bb'$, is refracted as it passes through entry surface 31 and is then reflected by surface 13 to reach point $F_z$ of retina 5, located, in this case, away from the axis of the eye or from point F.

Figure 2D:
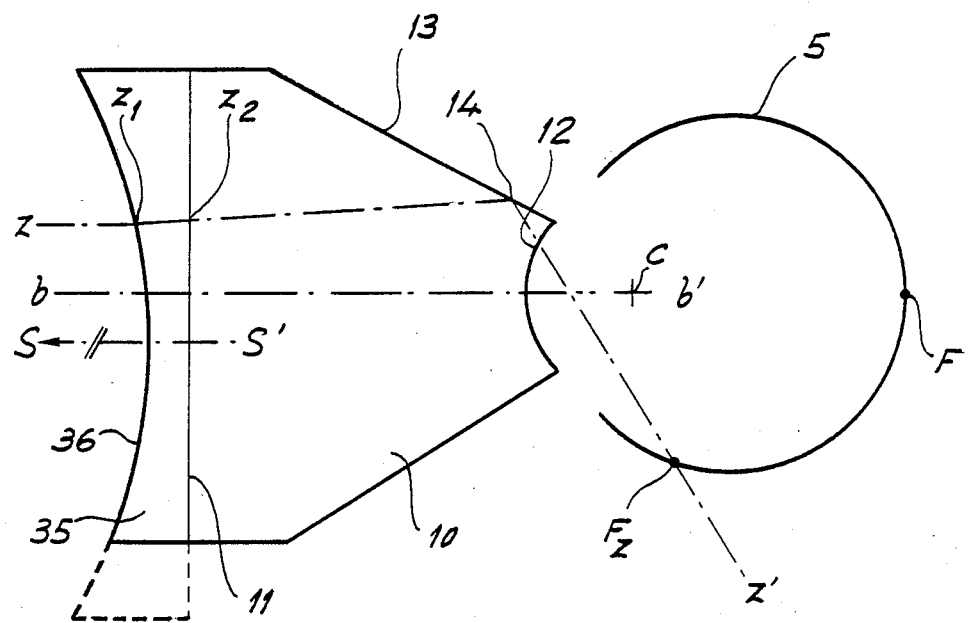

In the embodiment shown in FIG. 2d, at least a portion of a plano-concave lens 35, having a plane surface and a spherical surface 36, is used by way of compensating element. The plane surface of lens 35 is applied against the entry surface 11 of Goldmann lens 10 and its spherical surface 36, which constitutes the entry surface of the compensated contact lens arrangement, is defined, as in the previous case, by its centre of curvature S, which lies outside the Figure, and by its radius of curvature. If the same plastic material is used for both the compensating lens and the Goldmann lens, the Coddington equations show that the centre of curvature S of the compensating lens should be positioned approximately 2 mm away from axis $bb'$, on the side opposite surface 13, and that its radius of curvature should be roughly 75 mm long.

The path followed by an incident light beam, shown by its axis $zz'$, is also shown in FIG. 2d. The beam reaches surfaces 36 parallel to axis $bb'$, and, after being refracted at point $z_1$ and reflected at point 14 by surface 13 (the later having an appropriate slant), reaches retina 5 at point $F_z$.

The compensating element and the Goldmann lens may be made of the same material but as two different components. These two components, once assembled, enable a surface 11 to be physically defined in the contact lens arrangement thus obtained. This surface, however, has no effect on the light rays, as the refractive indices are the same on both sides of the surface. The compensated contact lens arrangement may therefore be made in one homogeneous piece within which surface 11 can no longer be located. This one-piece lens arrangement will of course have the same properties as the previous arrangement. Materials having different refractive indices may also be used for the compensating element and the Goldmann lens. The rays of incident light beam Z will then be refracted on reaching surface 11 or at point $z_2$ along axis $zz'$ of the beam.

I claim:

1. A contact lens arrangement for optically examining an eye and treating it with an incident light beam, the beam traveling a distance e inside the lens arrangement between an entry surface and an exit surface which is applied to the eye, and the eye producing for said beam an astigmatism defined by a sagittal focal distance S and a tangential focal distance T, the lens arrangement comprising:

a principal element for focusing said beam onto a working point on the retina inside the eye, said principal element having a refractive index n and being provided with a plane entry surface and an exit surface forming said lens arrangement exit surface, the axis of said beam being displaced from the optical axis of said principal element and perpendicular to said plane entry surface thereof; and a compensating element having a refractive index n and a plane exit surface which is coupled with the plane entry surface of the principal element, said compensating element being provided with an entry surface forming said lens arrangement entry surface such that a plane tangent to said entry surface of the compensating element, at the point where the axis of said beam strikes the lens arrangement, is inclined with respect to the plane entry surface of the principal element by an angle which is selected on the basis of e, S, T and n so as to produce for said beam an astigmatism opposite to that of the eye.

2. A contact lens arrangement as in claim 1, wherein the principal element is a Goldmann lens comprising a plane entry surface, a spherical exit surface having an axis of symmetry perpendicular to the plane entry surface and passing through the center of curvature of the exit surface, and a reflecting surface on which the beam is reflected inside said principal element between the plane entry surface and the spherical exit surface thereof.

3. A contact lens arrangement as in claim 2, wherein the compensating element is a prism.

4. A contact lens arrangement as in claim 2, wherein the compensating element is at least a portion of a plano-convex lens having an axis of symmetry.

5. A contact lens arrangement as in claim 2, wherein the compensating element is at least a portion of a plano-concave lens having an axis of symmetry.

6. A contact lens arrangement as in claim 4, wherein the axis of symmetry of the compensating element and the axis of symmetry of the exit surface of the Goldmann lens are parallel and offset one with respect to the other.

7. A contact lens arrangement as in claim 5, wherein the axis of symmetry of the compensating element and the axis of symmetry of the exit surface of the Goldmann lens are parallel and offset one with respect to the other.

8. A contact lens arrangement as in claim 1, wherein the principal element and the compensating element are formed by a single, homogeneous part.

9. A contact lens arrangement as in claim 1, wherein said angle of inclination is defined substantially by the following relationship:

arc sin $[(T-S) / (T+e-(S+e)/n^2)]^{\frac{1}{2}}$.

* * * * *